United States Patent
Uihlein (10) Patent No.: US 9,345,500 B2
(45) Date of Patent: May 24, 2016

(54) MANUALLY ACTUATED FUNCTION HOSE INSTRUMENT AND OPERATING DEVICE THEREFOR

(75) Inventor: Bernhard Uihlein, Dettingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 436 days.

(21) Appl. No.: 13/583,463

(22) PCT Filed: Mar. 4, 2011

(86) PCT No.: PCT/EP2011/053297
§ 371 (c)(1),
(2), (4) Date: Oct. 17, 2012

(87) PCT Pub. No.: WO2011/110493
PCT Pub. Date: Sep. 15, 2011

(65) Prior Publication Data
US 2013/0035695 A1    Feb. 7, 2013

(30) Foreign Application Priority Data
Mar. 9, 2010    (DE) .......................... 10 2010 010 798

(51) Int. Cl.
*A61B 17/22*     (2006.01)
*A61B 17/221*    (2006.01)
*A61B 1/00*      (2006.01)
(Continued)

(52) U.S. Cl.
CPC ........... *A61B 17/221* (2013.01); *A61B 1/00066* (2013.01); *A61B 1/018* (2013.01); *A61B 2017/00477* (2013.01)

(58) Field of Classification Search
CPC ................. A61B 17/221; A61B 1/018; A61B 2017/00477; A61B 17/22; A61B 17/29; A61B 17/2909; A61M 29/00; A61M 25/09025
USPC ................... 606/127, 159, 191; 600/184, 585
See application file for complete search history.

(56) References Cited

U.S. PATENT DOCUMENTS 5,281,230 A * 1/1994 Heidmueller ................. 606/127
5,779,686 A    7/1998 Sato et al.
(Continued)

FOREIGN PATENT DOCUMENTS

DE           23 25 404 A1    11/1974
WO    WO 2010/133245 A1    11/2010

OTHER PUBLICATIONS

German Office Action dated Jan. 26, 2011 (four (4) pages).
(Continued)

*Primary Examiner* — Victor Nguyen
(74) *Attorney, Agent, or Firm* — Crowell & Moring LLP (57) ABSTRACT

A manually actuated function hose instrument has a hose-shaped function part and a wire-shaped function part extending in the latter, wherein the two function parts are axially movable relative to each other in order to exert a useful function at a distal section remote from a proximal end section. An associated operating device, which has two operating parts, is arranged at the proximal end section of the function parts. A fixing part is provided which serves for the external fixing of the operating device and with which the second operating part is coupled in an axially relatively movable manner, and/or the second operating part is connected non-releasably to the proximal end section of the hose-shaped function part and contains an operating ring with a circumferential finger recess as operating area.

17 Claims, 5 Drawing Sheets

(51) Int. Cl.
*A61B 1/018* (2006.01)
*A61B 17/00* (2006.01)

(56) References Cited

U.S. PATENT DOCUMENTS

| | | |
|---|---|---|
| 2005/0113862 A1 | 5/2005 | Besselink et al. |
| 2005/0182292 A1 | 8/2005 | Suzuki |
| 2007/0255311 A1 | 11/2007 | Hiraoka |
| 2007/0270640 A1 | 11/2007 | Dimitriou et al. |
| 2008/0242925 A1 | 10/2008 | Suda |
| 2012/0088972 A1 | 4/2012 | Pinkowski et al. |

OTHER PUBLICATIONS

International Search Report dated Jun. 8, 2011, including English translation (six (6) pages).
International Preliminary Report on Patentability (Form PCT/IB/338 & Form PCT/IB/373) dated Oct. 4, 2012 (two (2) pages).
Written Opinion (Form PCT/ISA/237) (four (4) pages).

* cited by examiner

Fig. 9

MANUALLY ACTUATED FUNCTION HOSE INSTRUMENT AND OPERATING DEVICE THEREFOR

BACKGROUND AND SUMMARY OF THE INVENTION

The invention relates to a manually actuated functional hose instrument with a hose-shaped functional part and with a wire-shaped functional part extending in the latter, wherein the two functional parts are axially movable relative to each other in order to perform a useful function at a distal section remote from a proximal end section, and the invention also relates to an associated operating device. The operating device has a first operating part, which is connected to the proximal end section of the wire-shaped functional part and has an operating head at the proximal end of the wire-shaped functional part, and a second operating part, which is connected to the proximal end section of the hose-shaped functional part and has an operating area lying at an axial distance in front of the operating head.

In the present context, a hose-shaped functional part is to be understood generally as any elongate hose or tube structure that has a hollow channel for the passage of the wire-shaped functional part. In the present context, a wire-shaped functional part is to be understood as any elongate component that is received in the hollow channel of the hose-shaped part so as to be axially movable relative thereto and that is made of a solid or hollow metal or plastic material.

Manually actuated functional hose instruments of this kind are customary, for example, in the field of endoscopic medicine, especially in the form of stone-catching basket instruments with a deployable wire basket for collecting stones or the like in tissue spaces, and similar instruments such as wire filter instruments, wire loop instruments and collecting net instruments. In these known uses, a deployable element such as the wire basket, a wire filter, a wire loop or a collecting net is typically arranged at the distal end of the wire-shaped functional part, and, by moving the wire-shaped functional part axially back and forth relative to the hose-shaped functional part surrounding it, this element is collapsed and drawn into the distal end of the hose-shaped functional part or is moved out of the latter and deployed.

A similar use concerns guide wire units for catheter instruments, where the wire-shaped functional part is a so-called tension wire, and the hose-shaped functional part is a hose surrounding the latter, which hose is connected to the tension wire in the distal area. By axial relative movement of tension wire and hose, a distal section of the guide wire unit can be deformed in a desired manner, e.g. bent, or a slotted distal section of the hose-shaped functional part can be axially shortened and in this way opened out like a wire basket.

Laid-open specification US 2005/0113862 A1 discloses a guide wire unit of this kind, in which the hose has, in the proximal end section, an area that is elastically compressible in the axial direction by means of a slit, and which guide wire unit has, in its proximal end section, an operating device. The latter comprises a first operating part, which acts with an operating head on the proximal end of the tension wire, and a second operating part, which is connected to the hose in front of the elastic area thereof. The second operating part has a grip sleeve with a screw clamp, by means of which it can be clamped firmly on the hose. The operating head has a blind bore, into which the proximal end of the wire-shaped functional part, with the proximal end of the hose surrounding the latter, is placed to the rear of the elastic area. A guide sleeve, formed integrally on the operating head and protruding axially in the distal direction, surrounds the proximal end section of wire-shaped functional part and hose-shaped functional part and is guided telescopically and axially movably in the grip sleeve.

It is an object of the invention to provide a manually actuated functional hose instrument of the type mentioned at the outset, which permits comparatively simple, ergonomic and reliable operation by one hand, and an operating device suitable therefor.

The invention achieves this object by providing an operating device which comprises a first operating part, which is connected to the proximal end section of the wire-shaped functional part and has an operating head at the proximal end of the wire-shaped functional part and a second operating part, which is connected to the proximal end section of the hose-shaped functional part and has an operating area lying at an axial distance in front of the operating head. According to a first aspect of the invention, a fixing part is further provided which serves for the external fixing of the operating device and to which the second operating part is coupled in a mutually axially movable manner. According to another aspect of the invention, the second operating part is connected non-releasably to the proximal end section of the hose-shaped functional part and has an operating ring with a circumferential finger recess as an operating area. The invention further provides a manually actuated functional hose instrument equipped with an operating device according to the invention.

The operating device according to the invention thus comprises a fixing part, to which the second operating part is coupled in an axially movable manner, and/or an operating ring with circumferential finger recess as second operating part, which is connected non-releasably to the hose-shaped functional part. Both measures, individually or in combination, ensure that the functional hose instrument can be operated comfortably and reliably, particularly using one hand, with the operating head being actuated by the thumb of one hand and the operating ring being held between two fingers, e.g. between index finger and middle finger, or between middle finger and ring finger, the fingers in question being placed in the finger recess of the operating ring. The finger recess serves as operating area and prevents the operating ring from accidentally slipping through the space between the two fingers holding it. The non-releasable connection, e.g. a bonded or welded connection, holds the operating ring securely on the hose-shaped functional part, without adversely affecting the axial mobility of the wire-shaped functional part in the hose-shaped functional part. The desired axial relative movement between wire-shaped functional part and hose-shaped functional part can be achieved very easily by actuation of the operating head using a thumb.

The fixing part allows the operating device to be fixed to an external component, e.g. to an endoscope in the case of a corresponding medical endoscopy instrument. The second operating part can be moved axially relative to the fixing part, e.g. by corresponding actuation of the operating ring. Thus, for example in the case of a medical functional hose instrument, such as a stone-catching basket instrument or the like, inserted into an endoscope channel, the hose-shaped functional part, and possibly also the wire-shaped functional part in synchrony therewith, can be moved axially back or forth in the endoscope channel.

In a development of the invention, the first operating part is connected to the wire-shaped functional part for rotation therewith and is movable in rotation with respect to the second operating part. This measure makes it possible to rotate the wire-shaped functional part relative to the hose-shaped functional part, preferably freely in rotation without any limit on the rotation angle, by turning the first operating part correspondingly relative to the second operating part and, therefore, to the hose-shaped functional part connected non-releasably to the latter. This can also still be done by one-handed operation. Alternatively, the user can use his other hand for this purpose.

In a development of the invention, the first operating part is guided telescopically on the second operating part by means of guide sleeves that are suitably guided one inside the other. This permits an advantageous and reliable actuation of the two operating parts relative to each other, in order to obtain the desired axial relative movement of the two functional parts. In another embodiment, a helical spring is provided, which acts in the axial direction between the two operating parts and which surrounds the proximal end section both of the wire-shaped functional part and also of the hose-shaped functional part and bears at one end on the operating head and at the other end on the guide sleeve of the second operating part. Thus, in a manner that is advantageous in terms of design and function, the two functional parts can be pretensioned by pressure or tension into an end position of their axial relative mobility, for example, in the case of a medical stone-catching basket instrument, into a starting position with the catching basket drawn into the hose-shaped functional part.

In a development of the invention, using two guide sleeves suitably guided one inside the other, a telescopic guidance of the second operating part on the fixing part is provided. In this way, the second operating part, and with it the hose-shaped functional part, can be moved axially back or forth in a functionally reliable manner relative to the fixing part, either with or without the first operating part and the wire-shaped functional part. In another embodiment, an elastic pretensioning element is provided, which acts in the axial direction between the fixing part and the second operating part, e.g. in the form of a corresponding helical spring. In this way, the hose-shaped functional part can be pretensioned with pressure or tension into a desired axial end position relative to the fixing part.

In a development of the invention, the fixing part has an attachment means for releasable mounting on an endoscope. This permits an advantageous use of the manually actuated functional hose instrument for endoscopic applications.

In a development of the invention, the first operating part is connected releasably to the wire-shaped functional part. It is thus possible, if need be, to release the first operating part from the wire-shaped functional part. This can be advantageous, for example in endoscopic applications, in order to be able to pull the first operating part, together with the second operating part and the hose-shaped functional part, proximally from the wire-shaped functional part.

The manually actuated functional hose instrument according to the invention advantageously has an operating device according to the invention for effecting the axial relative movement of hose-shaped functional part and wire-shaped functional part for the purpose of effecting the corresponding useful function. In particular, the instrument can be a stone-catching basket instrument, a wire filter instrument, a wire loop instrument or a collecting net instrument for endoscopic applications, as are known per se to a person skilled in the art. If so desired, the operating device can also be retrofitted on an otherwise conventional functional hose instrument.

BRIEF DESCRIPTION OF THE DRAWINGS

Advantageous embodiments of the invention are shown in the drawings and are described below. In the drawings.

DETAILED DESCRIPTION OF THE DRAWINGS

Figure 1:
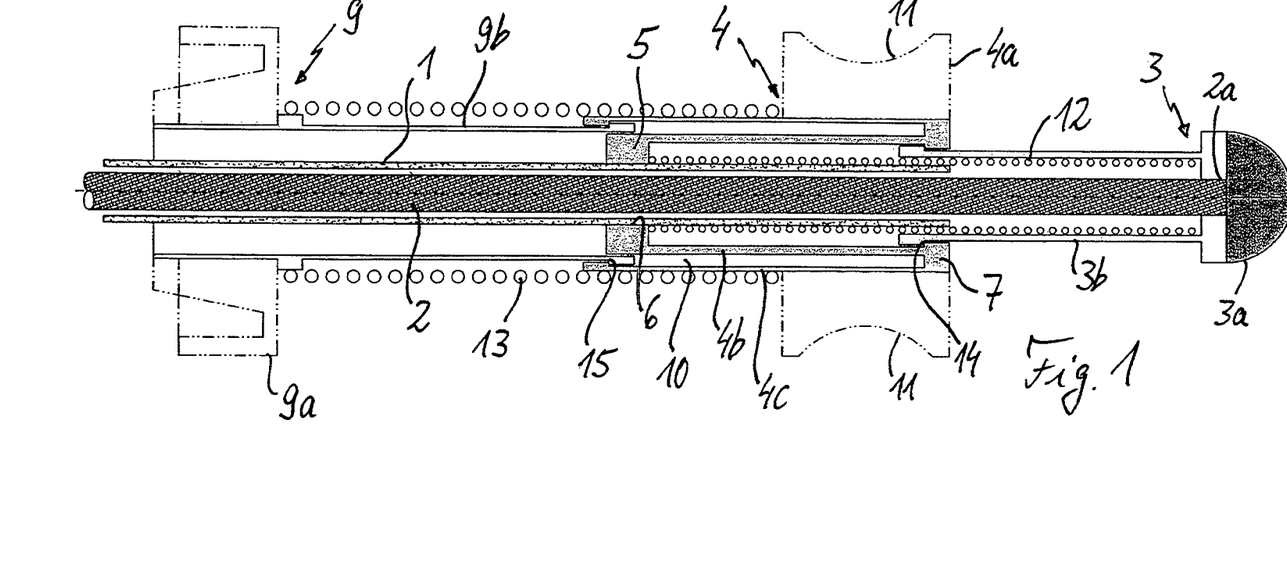
FIG. 1 shows a longitudinal section through an operating device for a manually actuated functional hose instrument in a pretensioned starting position.

The operating device shown in FIG. 1 serves for the manually actuated operation of a functional hose instrument that has a hose-shaped functional part 1 and a wire-shaped functional part 2 extending in the latter in a mutually axially movable manner, which parts are shown in FIG. 1 by their proximal end section. The axial relative mobility of the hose-shaped functional part 1, hereinafter also referred to in short as the hose, and of the wire-shaped functional part 2, hereinafter also referred to in short as the functional wire or tension wire, serves to perform a useful function at a distal section of the instrument remote from the proximal end section; this does not necessarily have to be the distal end section, and instead it can also be a section of the two functional parts 1, 2 that lies between the proximal end section and a distal end section. Hose 1 and functional wire 2 can be made of any suitable solid or hollow plastic or metal materials, as are known per se to a person skilled in the art for the intended use of the particular functional hose instrument. Depending on the requirements, the hose 1 can be more flexible or stiffer than the functional wire 2.

The operating device shown has a first operating part 3, which is connected rigidly and non-releasably to the functional wire 2, and a second operating part 4, which is connected rigidly and non-releasably to the hose 1. The first operating part 3 has an operating head 3a, which directly adjoins a proximal end 2a of the functional wire 2, it being connected to the latter in a non-releasable manner, e.g. by a bonded or welded connection. The first operating part 3 further comprises an operating head guide sleeve 3b, which is integrally formed on the operating head 3a and protrudes axially from the latter in the distal direction, i.e. to the left in FIG. 1. The second operating part 4 has an operating ring 4a, and an operating ring guide sleeve 4b which, together with the operating head guide sleeve 3b, forms a guide means of the telescopic type, by means of which the two operating parts 3, 4 are guided on each other in a mutually axially movable manner. Furthermore, the two operating parts 3, 4 are thereby freely rotatable with respect to each other about their common longitudinal center axis. The operating head guide sleeve 3b protrudes in the proximal direction, i.e. rearward, from the operating ring guide sleeve 4b, such that the operating head 3a is located at an axial distance behind the operating ring 4a.

At its distal face 5, the operating ring guide sleeve 4b is provided with a central bore 6, through which the two functional parts 1, 2 are guided. On the inner edge of its bore 6, the operating ring guide sleeve 4b is connected fixedly and non-releasably to the hose 1, e.g. by a bonded or welded connection. At its proximal face 7, the operating ring guide sleeve 4b is connected fixedly to the operating ring 4a, preferably by means of operating ring 4a and operating ring guide sleeve 4b being produced as a one-piece component.

Furthermore, the operating device shown has a fixing part 9, which serves for the external fixing of the entire operating device, i.e. for fixing the latter on an external component, for example on an endoscope component in the case of a medical use of the functional hose instrument in endoscopy. The fixing part 9 has an attachment part 9a, in the example shown a conventional Luer connector, and a fixing part guide sleeve 9b that extends axially from the attachment part 9a in the proximal direction. Correspondingly thereto, the second operating part 4 has another and outer operating ring guide sleeve 4c, which coaxially surrounds the inner operating ring guide sleeve 4b to form an annular gap 10. The fixing part guide sleeve 9b cooperates with the outer operating ring guide sleeve 4c to form a guide means of the telescopic type for guiding the second operating part 4 on the fixing part 9 in a mutually axially movable manner. The fixing part guide sleeve 9b is received in the annular gap 10 between inner and outer operating ring guide sleeve 4b, 4c.

As is shown, the operating ring 4a has, on its outer periphery, a circumferential and semicircular recess 11 which functions as a finger recess and thus contributes to an ergonomic and reliable actuation of the operating device by a user. This can be done preferably, or as far as possible, using one hand, with the user positioning the operating ring 4a between two neighboring fingers, which he places in a respective area of the finger recess 11, e.g. between index finger and middle finger, or between middle finger and ring finger, after which he presses the operating head 3a with his thumb and thus moves the first operating part 3 with the functional wire 2 relative to the second operating part 4 with the hose 1. Compared to illustrative embodiments of the invention in which the second operating part does not have any such finger recess, the illustrative embodiments with finger recess ensure a better hold of the second operating part by two neighboring fingers of one hand. Alternatively to the circumferentially extending finger recess mentioned, it suffices, in alternative illustrative embodiments of the invention, to design the finger recess in the form of two circumferentially opposite recess areas of a suitably modified operating ring, in which recess areas the two neighboring fingers can be placed.

Preferably, one or more elastic pretensioning elements are present, in order to ensure that the mutually axially movable components are kept pretensioned in an axial end position by pressure or tension, from which end position they can then be moved by active user actuation. For this purpose, in the example shown in FIG. 1, a first helical compression spring 12 is provided between first and second operating parts 3, 4, and a second helical compression spring 13 is provided between second operating part 4 and fixing part 9. The first helical compression spring 12 surrounds the proximal end section both of the functional wire 2 and also of the hose 1, by extending in an annular gap between the hose 1 and the operating head guide sleeve 3b, and it bears axially at one end on the distal face 5 of the inner operating ring guide sleeve 4b and at the other end on the operating head 3a. In this way, the helical compression spring 12 pretensions the first operating part 3 with pressure into an extended position of its telescopic guide on the second operating part 4, i.e. into a position in which the functional wire 2 is drawn back relative to the hose 1. Analogously, the other helical compression spring 13 pretensions the second operating part 4 with pressure into an extended position of its telescopic guide on the fixing part 9, in which position it surrounds the two associated guide sleeves 9b, 4c and bears axially at one end on the attachment part 9a and at the other end on the operating ring 4a.

The end positions, into which the respective components of the operating device are pretensioned by the two helical compression springs 12, 13, are defined by suitable limit stops of the telescopic guide sleeves. In particular, the drawn-back end position of the first operating part 3 is defined by a corresponding limit stop 14 of the distal end section of the operating head guide sleeve 3b on the proximal end section of the inner operating ring guide sleeve 4b, and the pushed-back end position of the second operating part 4 relative to the fixing part 9 is defined by a corresponding limit stop 15 of the proximal end section of the fixing part guide sleeve 9b on the distal end section of the outer operating ring guide sleeve 4c.

Hereinafter, the advantageous operation of a manually actuated functional hose instrument equipped with the operating device from FIG. 1 is discussed in more detail in connection with FIGS. 2 to 8, which depict typical operating situations. A medical stone-catching basket instrument is taken here as an example of a manually actuated functional hose element. It will be appreciated, however, that the invention similarly covers any other manually actuated functional hose instruments which are intended for medical and non-medical uses and which are equipped with such an operating device. Examples of medical uses that may be mentioned here are, in particular, wire filter instruments, wire loop instruments and collecting net instruments. FIGS. 2 to 8 also depict, by way of example, the situation where the functional hose instrument or stone-catching basket instrument is fixed, via the attachment part 9a of the fixing part 9 of the operating device, to a proximal end of an endoscope channel 16, of which only a short section is represented schematically in each of FIGS. 2, 3, 5 and 7 and which can be formed, for example, by an endoscope tube with a proximal endoscope attachment part.

Figure 2:
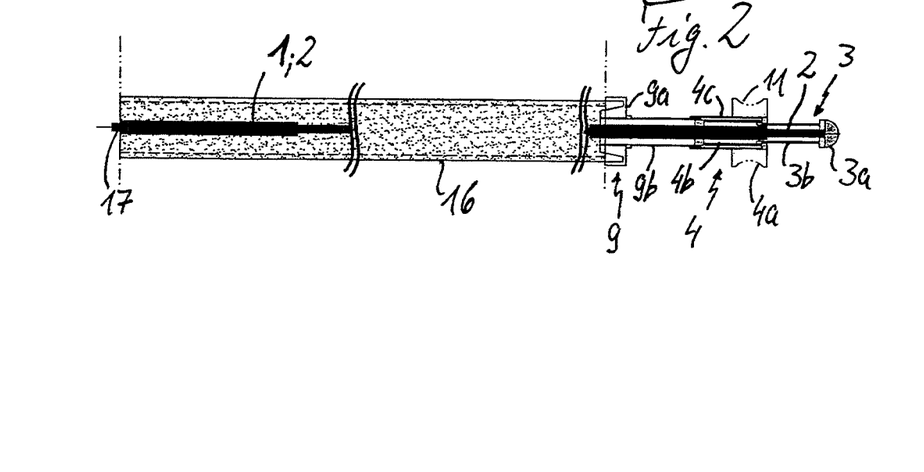
FIG. 2 shows a short longitudinal section through a medical stone-catching basket instrument with the operating device from FIG. 1 mounted on an endoscope channel.

FIG. 2 shows the functional hose instrument or stone-catching basket instrument in a starting position in the endoscope channel 16, which position corresponds to the pretensioned position of the operating device as shown in FIG. 1. To make matters clearer, the pretensioning spring elements 12, 13 have been omitted in the views in FIGS. 2 to 8. In the starting position in FIG. 2, a catching basket 17 arranged at the distal end of the functional wire 2 is in a collapsed state and drawn back into the distal end section of the hose 1.

Figure 3:
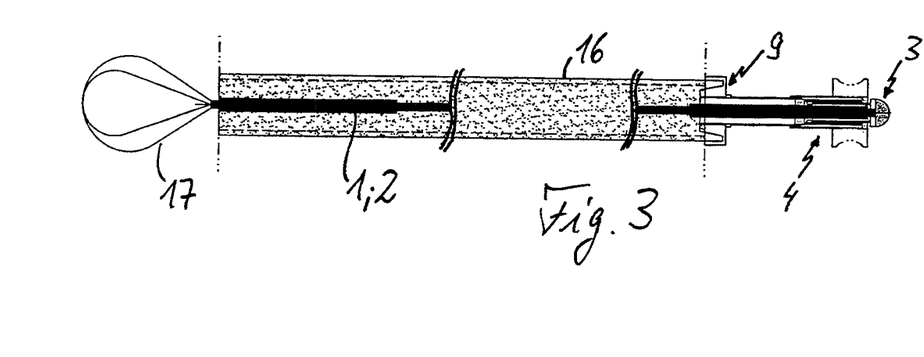
FIG. 3 shows the view of the instrument according to FIG. 2 in a functional position with deployed catching basket.
Figure 4:
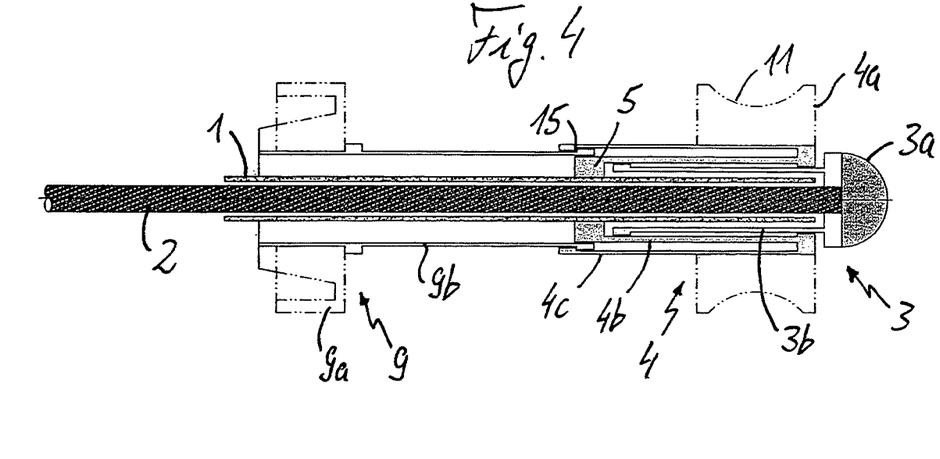
FIG. 4 shows a detail of the operating device for the functional position from FIG. 3.

By pressing on the operating head 3a, e.g. with the thumb, while securely holding the operating ring 4a in the one-handed operation described above, it is possible for the functional wire 2 to be pushed forward relative to the hose 1 into the functional position shown in FIG. 3, as a result of which the wire basket 17 moves out from the hose 1 and automatically deploys. This functional end position can be defined, for example, by the operating head 3a coming into abutment against the operating ring 4a or the corresponding operating ring guide sleeve 4b and/or by the operating head guide sleeve 3b coming into abutment with its distal face against the distal end area 5 of the corresponding operating ring guide sleeve 4b. For this purpose, the course of the axial relative mobility between the two operating parts 3, 4 corresponds at least to the axial length by which the wire basket 17 is to move out of the hose 1. The detail view in FIG. 4 shows more clearly the position of the operating device, which corresponds to the functional position of the stone-catching basket instrument according to FIG. 3.

Figure 5:
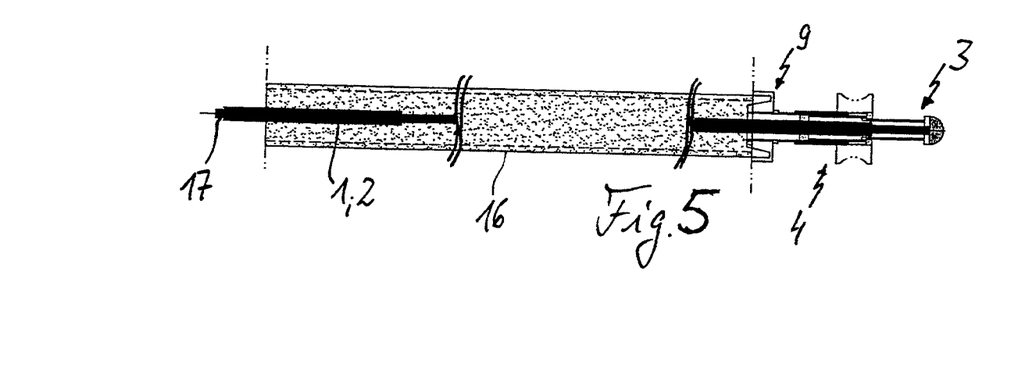
FIG. 5 shows the view of the instrument according to FIG. 2 in a pushed-forward starting position.
Figure 6:
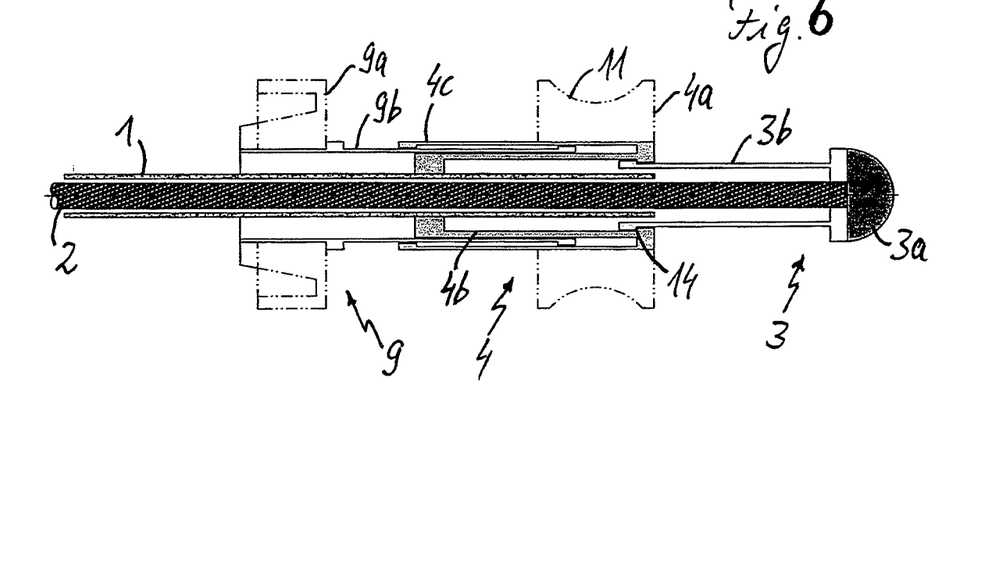
FIG. 6 shows a detail of the operating device according to FIG. 4 for the pushed-forward starting position from FIG. 5.

FIGS. 5 and 6 illustrate a situation in which the entire stone-catching basket instrument, i.e. hose 1 and tension wire 2, is pushed forward in the endoscope channel 16, for example in order to collect a stone farther away from the distal end of the endoscope channel 16. To do this, the user pushes the second operating part 4 with operating ring 4a distally forward onto the fixing part 9. FIGS. 5 and 6 show, in particular, the instrument in a position in which the telescopic guide has in this way been pushed together by slightly more than half between second operating part 4 and fixing part 9. The first operating part 3 is thus also moved forward synchronously with the second operating part 4 and, in the corresponding end position, is held pretensioned on the second operating part 4. Hose 1 and tension wire 2, with catching basket 17 drawn at the distal end into the hose 1, are therefore moved forward synchronously in the endoscope channel 16 until the distal end of the instrument has reached a desired position in front of the endoscope channel 16.

Figure 7:
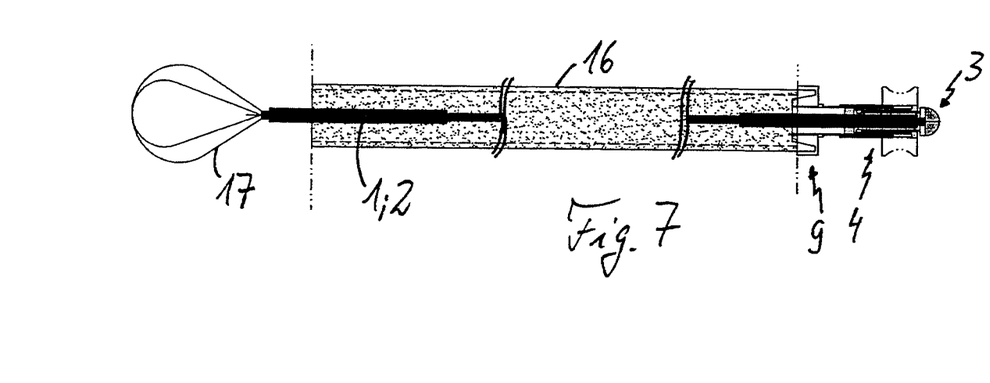
FIG. 7 shows the view of the instrument according to FIG. 5 in a functional position with deployed catching basket.
Figure 8:
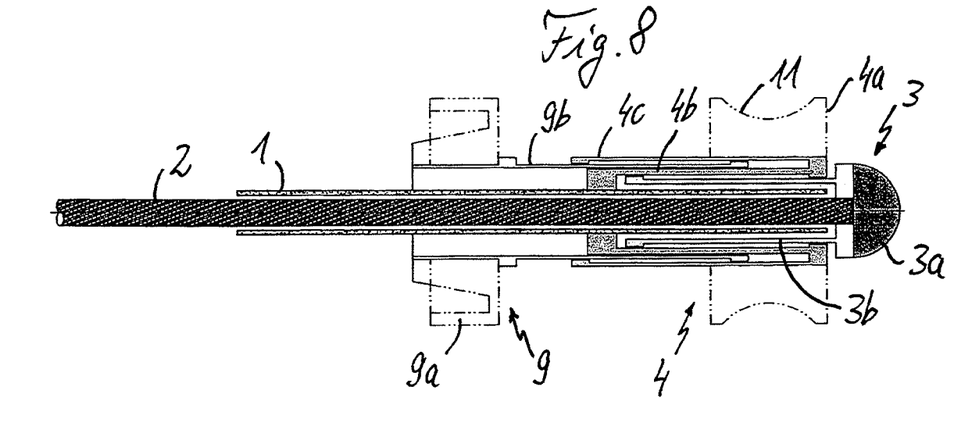
FIG. 8 shows a detail of the operating device according to FIG. 6 for the functional position from FIG. 7.

In this instrument position, the user can then deploy the catching basket 17 by holding the operating ring 4a securely and pressing on the operating head 3a until the catching basket 17 has emerged from the distal end section of the hose 1, as has been explained above with reference to FIG. 3. FIGS. 7 and 8 show the instrument in this pushed-forward state with automatically deployed catching basket 17. As is clear from FIG. 8, the operating head 3a in this position, compared to the situation in FIG. 6, is located in its position adjacent to the operating ring 4a in accordance with FIG. 4.

In the position with the catching basket 17 deployed as in FIG. 3 or FIG. 7, the user is able to collect a stone or a similar tissue particle. If need be, the user can rotate the catching basket 17 in order to make collecting the stone or particle easier. For this purpose, the first operating part 3, which is connected rigidly to the functional wire 2 and therefore also rotates therewith, simply has to be rotated via its operating head 3a or guide sleeve 3b. The user is also generally able to do this by the one-handed operation described. If need be, the user can use his other hand to rotate the first operating part 3. As has already been mentioned above, the first operating part 3 is held freely rotatably on the second operating part 4. It will be noted that, during this rotation movement, the functional wire 2 rotates in the hose 1, which in this case does not have to rotate too. Problems associated with a rotation movement of the hose 1 in the endoscope channel 16, for example increased frictional effects, etc., can thus be avoided.

As soon as the stone or particle has been collected, the user releases the pressure on the operating head 3a, as a result of which the latter is pressed back by means of the associated helical compression spring 12. In this way, the tension wire 2 is moved back relative to the hose 1, and the catching basket 17 is drawn partially into the hose 1 until it has been closed together to such an extent that it securely encapsulates the collected stone or particle. In this position, the entire instrument can then be withdrawn, along with the collected stone, from the tissue channel in question.

Figure 9:
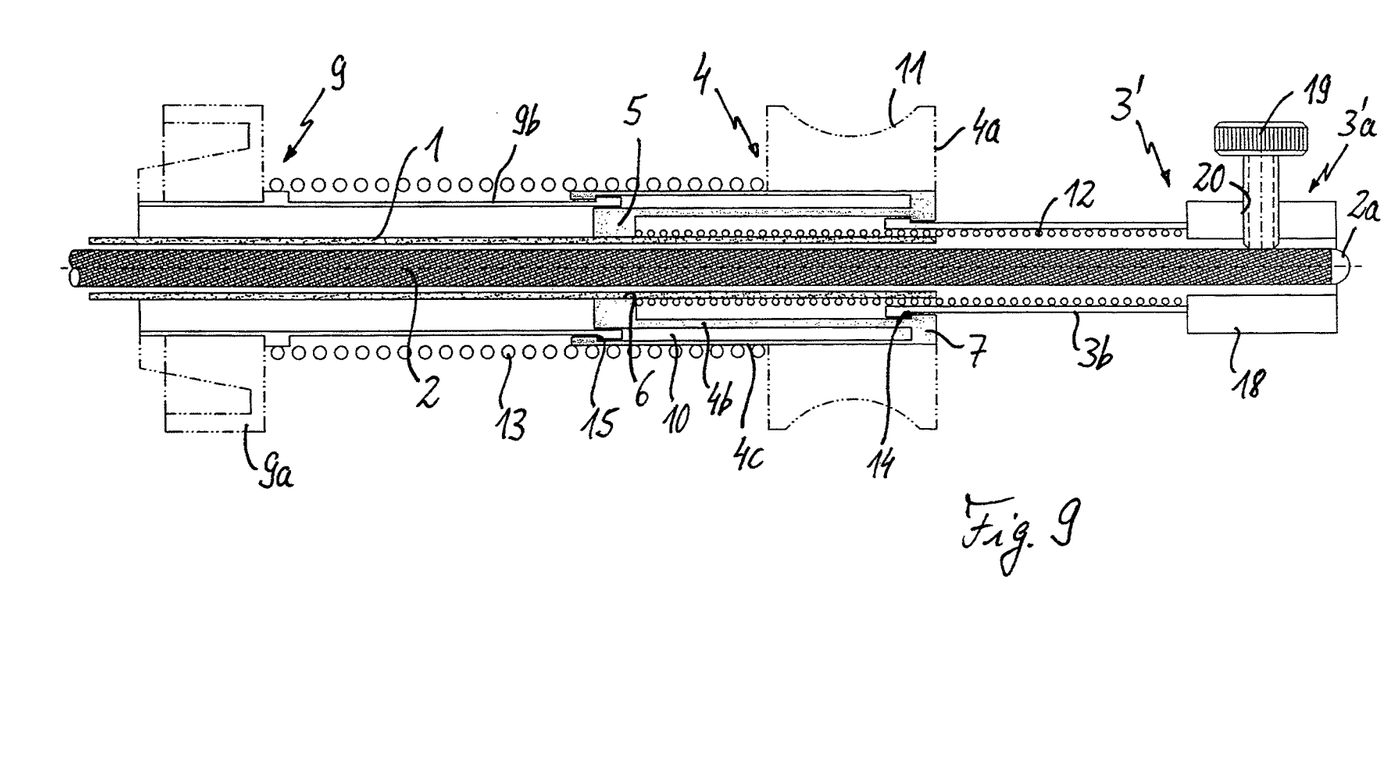
FIG. 9 shows a longitudinal section according to FIG. 1 for a modified operating device with releasable connection of operating head and wire-shape functional part.

FIG. 9 shows a variant with a modified first operating part 3', specifically a modified operating head 3'a, the operating device in FIG. 9 otherwise corresponding in design and function to that in FIGS. 1 to 8, and the same reference signs have been chosen in FIG. 9 for identical or functionally equivalent components, such that reference may be made in this respect to the above discussion of the operating device in FIGS. 1 to 8. The operating device in FIG. 9 differs from the one in FIGS. 1 to 8 in that the connection of operating head 3'a and functional wire 2 is releasable. For this purpose, the operating head 3'a has an operating head sleeve 18 and a locking screw 19, which is screwed into a radial bore 20 of the operating head sleeve 18. The operating head sleeve 18 surrounds the proximal end area of the functional wire 2, the operating head guide sleeve 12 protrudes from the distal front end of the operating head sleeve 18, and the proximal front end of the latter terminates substantially flush with the proximal end 2a of the functional wire 2, which proximal end is hemispherical in this example. When the locking screw 19 is tightened, the operating head 3'a is clamped on the proximal end area of the functional wire 2. The instrument is actuated by pressing, e.g. with the thumb, on the proximal front end of the operating sleeve 18, in which case the exposed hemispherical end 2a of the functional wire 2 is also available as operating surface.

The releasable connection of operating head 3'a and functional wire 2 has advantages, for example in the case where the stone-catching basket instrument has collected a stone in the distal wire basket, but it turns out that the stone is too big to be able to be removed by pulling the instrument out of the endoscope channel. In this case, in the instrument equipped with the operating device of FIG. 9, the clamping connection of the first operating part 3' on the functional wire 2 can be released by loosening the tightening screw 19. After the fixing of the operating device on the endoscope channel has been undone by correspondingly releasing the attachment part 9a, the entire operating device with the first operating part 3', second operating part 4 and fixing part 9, and with the hose 1 fixed on the second operating part 4, can be pulled back proximally and off of the functional wire 2. If need be, the releasable connection of first operating part 3' and functional wire 2 can of course also be used to remove only the first operating part 3', for which purpose the telescopic connection of the guide sleeves 4b, 12 between the first operating part 3' and the second operating part 4 is additionally uncoupled.

The above illustrative description of the operation of a medical stone-catching basket instrument makes clear that, by virtue of the operating device according to the invention, a suitably equipped functional hose element can be actuated very advantageously by hand, preferably and as far as possible by just one hand. For this purpose, the user holds the operating ring 4a between two neighboring fingers and actuates the operating head 3a with the thumb. By moving the operating ring 4a axially back and forth relative to the fixing part 9, it is possible for the entire instrument, i.e. the hose-shaped functional part and the wire-shaped functional part, to be moved back and forth synchronously relative to an external component on which the instrument is fixed by its fixing part. By pressing on the operating head 3a while keeping the operating ring 4a secure, the user can perform a desired useful function in the distal section of the instrument. In any case, he does not need help from another person for any part of the operation of the instrument.

It will be appreciated that the advantageous effects and properties explained above for the operation of a medical stone-catching basket instrument apply in the same way for the operation of other manually actuated functional hose instruments that are equipped with the operating device according to the invention.

The invention claimed is:

1. An operating device for a manually actuated functional hose instrument having a hose-shaped functional part and a wire-shaped functional part extending in the latter, wherein the two functional parts are axially movable relative to each other in order to perform a useful function at a distal section remote from a proximal end section of the functional parts, said operating device comprising:

a first operating part, which is connected to the proximal end section of the wire-shaped functional part and has an operating head at the proximal end of the wire-shaped functional part, a second operating part, which is connected to the proximal end section of the hose-shaped functional part and has an operating area lying at an axial distance in front of the operating head, and a fixing part, which serves for the external fixing of the operating device and to which the second operating part is coupled in a mutually axially movable manner, wherein the second operating part is guided telescopically on the fixing part, for which purpose the fixing part and the second operating part have two guide sleeves guided one inside the other.

2. The operating device as claimed in claim 1, wherein the second operating part is connected non-releasably to the proximal end section of the hose-shaped functional part and has an operating ring with a circumferential finger recess as an operating area.

3. The operating device as claimed in claim 1, wherein the first operating part is connected to the wire-shaped functional part for rotation therewith and is movable in rotation with respect to the second operating part.

4. The operating device as claimed in claim 3, wherein the first operating part is guided telescopically on the second operating part, for which purpose the two operating parts have two guide sleeves guided one inside the other.

5. The operating device as claimed in claim 4, further comprising a helical spring, which acts in the axial direction between the two operating parts and which surrounds the proximal end section of the wire-shaped functional part and of the hose-shaped functional part and bears at one end on the operating head and at the other end on the guide sleeve of the second operating part.

6. The operating device as claimed in claim 1, further comprising an elastic pretensioning element, which acts in the axial direction between the fixing part and the second operating part.

7. The operating device as claimed in claim 1, wherein the fixing part has an attachment means for releasable mounting on an endoscope.

8. The operating device as claimed in claim 1, wherein the first operating part is connected releasably to the wire-shaped functional part.

9. An operating device for a manually actuated functional hose instrument having a hose-shaped functional part and a wire-shaped functional part extending in the latter, wherein the two functional parts are axially movable relative to each other in order to perform a useful function at a distal section remote from a proximal end section of the functional parts, said operating device comprising:

a first operating part, which is connected to the proximal end section of the wire-shaped functional part and has an operating head at the proximal end of the wire-shaped functional part, a second operating part, which is connected to the proximal end section of the hose-shaped functional part and has an operating area lying at an axial distance in front of the operating head, said second operating part being connected non-releasably, via a fixing part, to the proximal end section of the hose-shaped functional part and having an operating ring with a circumferential finger recess as an operating area, wherein the fixing part serves for the external fixing of the operating device and is coupled to the second operating part in a mutually axially movable manner, and the second operating part is guided telescopically on the fixing part, for which purpose the fixing part and the second operating part have two guide sleeves guided one inside the other.

10. The operating device as claimed in claim 9, wherein the first operating part is connected to the wire-shaped functional part for rotation therewith and is movable in rotation with respect to the second operating part.

11. The operating device as claimed in claim 10, wherein the first operating part is guided telescopically on the second operating part, for which purpose the two operating parts have two guide sleeves guided one inside the other.

12. The operating device as claimed in claim 11, further comprising a helical spring, which acts in the axial direction between the two operating parts and which surrounds the proximal end section of the wire-shaped functional part and of the hose-shaped functional part and bears at one end on the operating head and at the other end on the guide sleeve of the second operating part.

13. The operating device as claimed in claim 9, wherein the first operating part is connected releasably to the wire-shaped functional part.

14. A manually actuated functional hose instrument, comprising:

a hose-shaped functional part and a wire-shaped functional part extending in the latter, wherein the two functional parts are axially movable relative to each other in order to perform a useful function at a distal section remote from a proximal end section of the functional parts, and an operating device, which is arranged on the proximal end section of the functional parts, said operating device comprising:

a first operating part, which is connected to the proximal end section of the wire-shaped functional part and has an operating head at the proximal end of the wire-shaped functional part, a second operating part, which is connected to the proximal end section of the hose-shaped functional part and has an operating area lying at an axial distance in front of the operating head, and a fixing part, which serves for the external fixing of the operating device and to which the second operating part is coupled in a mutually axially movable manner, wherein the second operating part is guided telescopically on the fixing part, for which purpose the fixing part and the second operating part have two guide sleeves guided one inside the other.

15. The manually actuated functional host instrument as claimed in claim 14, wherein the instrument is one of a medical stone-catching basket instrument, a wire filter instrument, a wire loop instrument, and a collecting net instrument.

16. A manually actuated functional hose instrument, comprising:

a hose-shaped functional part and a wire-shaped functional part extending in the latter, wherein the two functional parts are axially movable relative to each other in order to perform a useful function at a distal section remote from a proximal end section of the functional parts, and an operating device, which is arranged on the proximal end section of the functional parts, said operating device comprising;

a first operating part, which is connected to the proximal end section of the wire-shaped functional part and has an operating head at the proximal end of the wire-shaped functional part, and a second operating part, which is connected to the proximal end section of the hose-shaped functional part and has an operating area lying at an axial distance in front of the operating head, said second operating part being connected non-releasably via a fixing part to the proximal end section of the hose-shaped functional part and having an operating ring with a circumferential finger recess as an operating area, wherein the fixing part serves for the external fixing of the operating device and is coupled to the second operating part in a mutually axially movable manner, and the second operating part is guided telescopically on the fixing part, for which purpose the fixing part and the second operating part have two guide sleeves guided one inside the other.

17. The manually actuated functional host instrument as claimed in claim 16, wherein the instrument is one of a medical stone-catching basket instrument, a wire filter instrument, a wire loop instrument or a collecting net instrument.

\* \* \* \* \*